United States Patent [19]

Spector

[11] 4,200,229
[45] Apr. 29, 1980

[54] AROMA-DISPENSING CARTRIDGE AND HOLDER ASSEMBLY

[76] Inventor: Donald Spector, 380 Mountain Rd., Union City, N.J. 07087

[21] Appl. No.: 971,379

[22] Filed: Dec. 20, 1978

[51] Int. Cl.² ............................................. A61L 9/04
[52] U.S. Cl. .............................. 239/57; 224/42.46 R; 239/289; 248/311.1 R
[58] Field of Search ........................ 222/187, 402.13; 224/42.45 R, 42.46 R, 273; 206/387; 220/408; 248/311.1 R; 239/34, 57, 145, 289

[56] References Cited

U.S. PATENT DOCUMENTS

| | | | |
|---|---|---|---|
| 959,111 | 5/1910 | Buckland | 239/57 X |
| 2,287,581 | 6/1942 | Walker | 224/42.46 R X |
| 2,721,098 | 10/1955 | Mangels | 239/57 X |
| 3,679,133 | 7/1972 | Sekiguchi et al. | 239/34 |
| 4,084,732 | 4/1978 | Dearling | 239/34 X |

Primary Examiner—Andres Kashnikow
Attorney, Agent, or Firm—Michael Ebert

[57] ABSTRACT

An aroma-dispensing cartridge and holder assembly for installation in an automobile interior or other location for charging the atmosphere thereof with a pleasing or stimulating fragrance. The holder is in the form of a receptacle that is attachable to the underside of an automobile dashboard, with its open mouth facing the front seat of the vehicle. The cartridge is constituted by a bottle which is receivable in the holder and is filled with a liquid scent, the bottle being closed by a stopper having a suction pump supported thereon. The pump includes a flexible pipe extending into the bottle to draw liquid therefrom and a spring-biased hollow plunger coupled to the pipe, the free end of the plunger projecting beyond the mouth of the holder and being coupled to an actuator head. The hollow plunger communicates with an internal head chamber occupied by an absorptive pad. Pressing in the head causes the plunger to make a forward stroke, thereby drawing liquid from the bottle and passing it through the plunger to spray the absorptive pad in the head. When the head is released, the plunger, under the action of its spring, makes a reverse stroke to return the head to its normal position. The internal chamber in the head is vented to emit an aroma from the liquid-permeated pad. The cartridge is replaceable, so that by providing a set of cartridges each having a different aroma, a user may select an aroma which suits his taste or other requirements.

10 Claims, 3 Drawing Figures

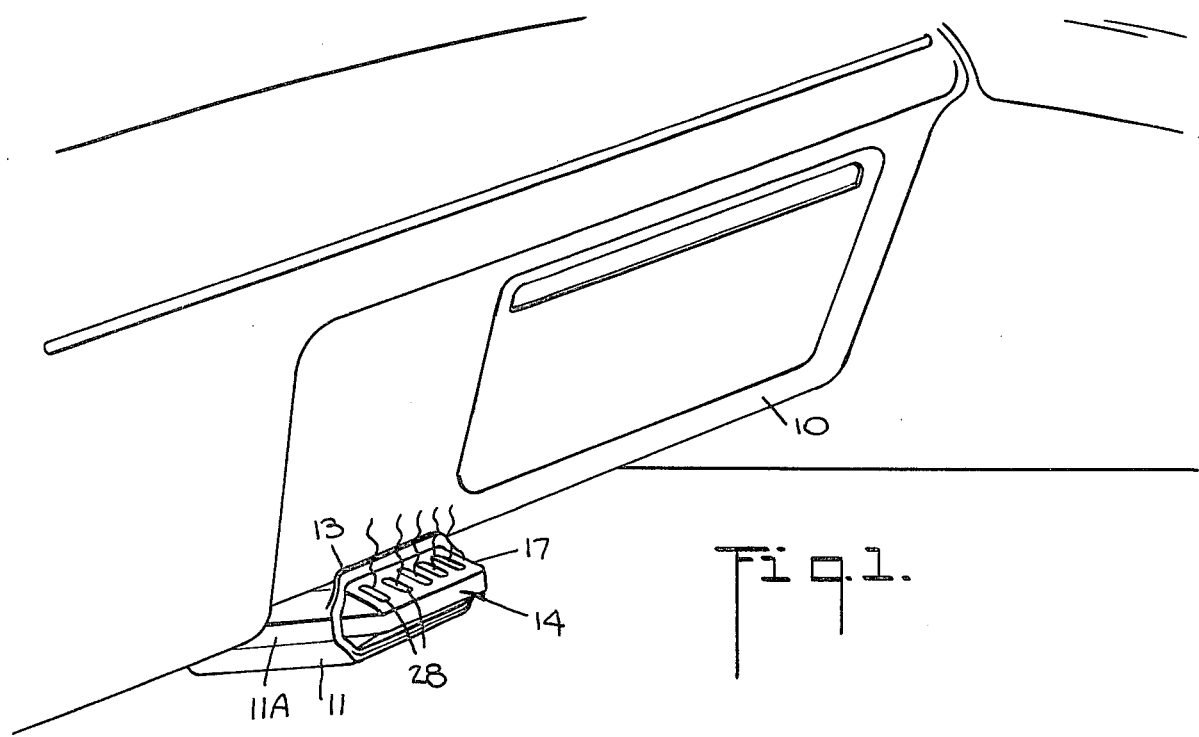
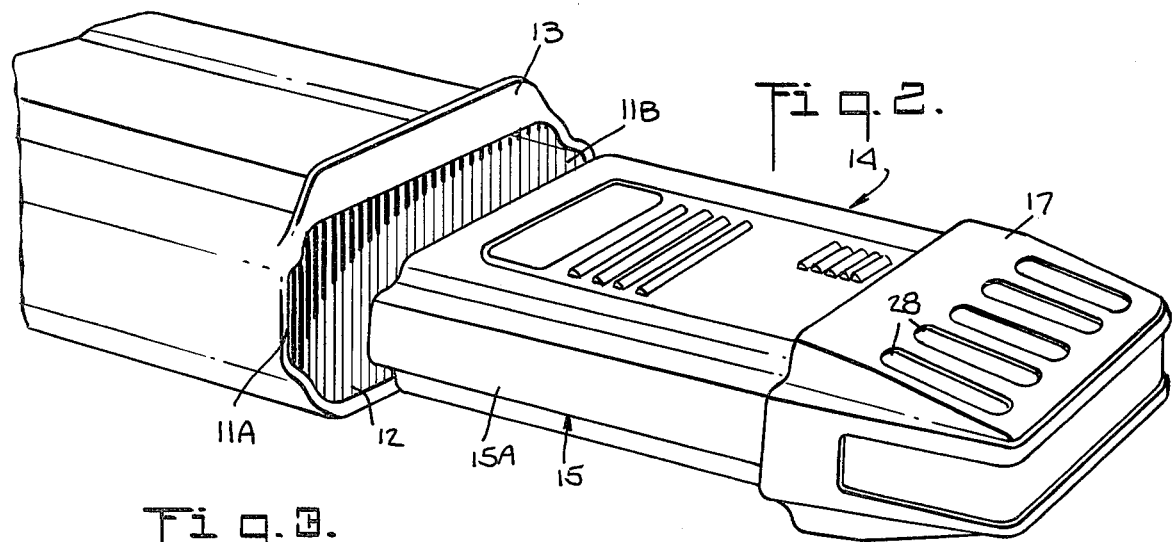
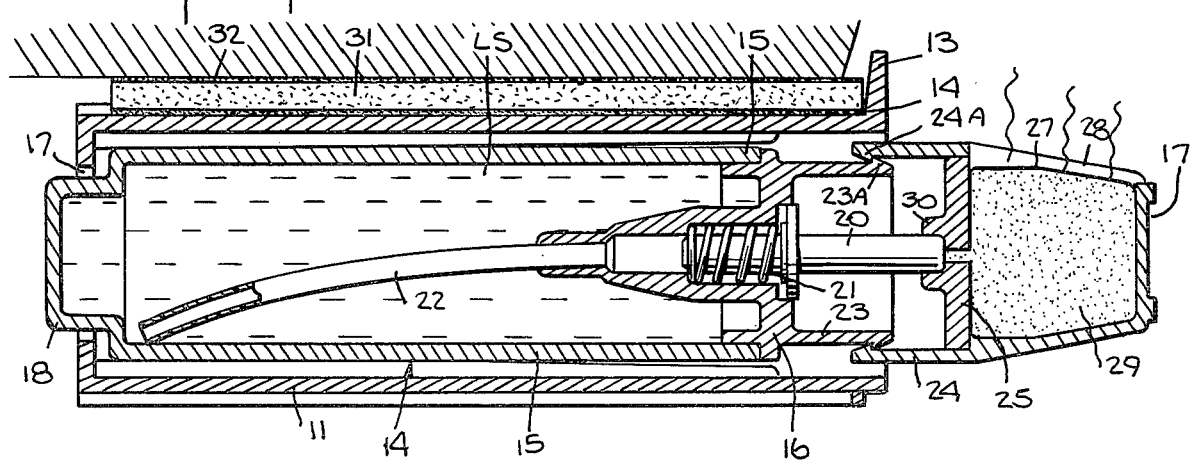

AROMA-DISPENSING CARTRIDGE AND HOLDER ASSEMBLY

BACKGROUND OF INVENTION

This invention relates generally to aroma dispensers, and in particular to an aroma-dispensing cartridge which is receivable within a holder mounted under the dashboard of an automobile whereby one may insert in the holder a cartridge emitting a selected aroma.

As used herein, the term "aroma" is not limited to pleasant or savory smells but encompasses scents that function as insecticides, air fresheners, deodorants or any other odor that acts to condition, modify or otherwise charge the atmosphere.

The aroma of perfumes and perfume-based products such as colognes and toilet waters was originally derived from the essential oils of plants. However, since the early 19th century, chemists have succeeded in analyzing many essential oils and in creating thousands of synthetics, some simulating natural products and others yielding altogether new scents. Perfumes today are largely blends of natural and synthetic scents and of fixatives which equalize vaporization and enhance pungency. In most liquid scents, the ingredients are combined with alcohol.

Various types of spray devices or dispensers are known for emitting aromas. Thus the patent to Dearling, U.S. Pat. No. 3,330,481, discloses a dispenser for wafting into the atmosphere an insecticide, a pleasant smelling scent or any other aroma, this being accomplished by means of a pressurized container. When the actuating button of this container is pressed, a dispersant is released onto an absorbent material, the absorbent dispersant permeating the atmosphere.

Similarly, the Sekiguchi et al. U.S. Pat. No. 3,679,133 discloses a perfume dispenser which includes a sponge-like head that receives and exudes a charge of perfume. In the spray aerosol can disclosed in the Harrison U.S. Pat. No. 3,972,473, an absorptive ring is impregnated with an air-freshening fragrance and released into the atmosphere. U.S. Pat. Nos. 1,921,821; 3,410,488 and 3,441,353 are along similar lines, for they show wicks and other absorptive materials to accept and emit a perfume or other odoriferous liquid.

While the prior art discloses various embodiments of aroma dispensers, none of these devices is particularly adopted for use in an automotive interior, an environment having special requirements. The atmosphere in most automobiles is somewhat unpleasant, for it is often permeated by exhaust and engine fumes, by odors emanating from the road, and in many cases by tobacco smoke. Hence it becomes desirable to mask or supplant these odors by more agreeable scents.

While a perfume odor may be desirable in a vehicle, since personal tastes differ and the choice of perfume may also depend on other variables, the availability of an aroma dispenser providing a single scent falls short of what is required. Moreover, in some instances, the aroma called for is not a perfume but a scent acting as a stimulant to keep the driver awake under driving conditions that may be soporific. Thus the type of pleasing scent that may be appropriate for a morning drive is usually not the same as that suitable for dusk; whereas when driving late at night, what then may be desirable is an odor, which, though perhaps unpleasant, functions to stimulate and awaken rather than relax the driver.

SUMMARY OF INVENTION

In view of the foregoing, it is the main object of this invention to provide an aroma dispenser which takes the form of a replaceable cartridge receivable in a stationary holder so that the user can insert therein whichever cartridge gives off an aroma suitable for a given occasion or satisfying a personal preference.

More particularly, an object of this invention is to provide cartridge and holder assembly of the above type wherein the holder can be mounted without tools under the dashboard of a vehicle and the cartridge may readily be inserted or withdrawn from the holder.

Also an object of this invention is to provide an aroma-dispensing cartridge which is activated simply by pressing and releasing the head thereof.

Briefly stated, these objects are accomplished by an aroma-dispensing cartridge and holder assembly in an automobile interior or other location for charging the atmosphere thereof with a pleasing or stimulating fragrance.

The holder is in the form of a receptacle that is attachable to the underside of an automobile dashboard, with its open mouth facing the front seat of the vehicle so that ready access thereto can be had by the driver or passenger. The cartridge is constituted by a bottle having a matching shape which is receivable in the holder and is filled with a liquid scent, the bottle being closed by a stopper having a suction pump supported thereon. The pump includes a flexible pipe extending into the bottle to draw liquid therefrom and a spring-biased hollow plunger coupled to the pipe, the free end of the plunger projecting beyond the mouth of the holder and being coupled to an actuator head.

The hollow plunger communicates with an internal head chamber occupied by an absorptive pad. Pressing in the head causes the plunger to make a forward stroke, thereby drawing liquid from the bottle and passing it through the plunger to spray the absorptive pad in the head. When the head is released, the plunger, under the action of its spring,, makes a reverse stroke to return the head to its normal position. The internal chamber in the head is vented to emit an aroma from the liquid-permeated pad. The cartridge is replaceable, so that by providing a set of cartridges each having a different aroma, a user may select an aroma which suits his taste or other requirements.

OUTLINE OF DRAWINGS

For a better understanding of the invention as well as other objects and further features thereof, reference is made to the following detailed description to be read in conjunction with the accompanying drawings, wherein:

FIG. 1 is a perspective view of an aroma-dispensing cartridge and holder assembly in accordance with the invention as installed under the dashboard of a vehicle;

FIG. 2 shows the cartridge being inserted in the holder; and

FIG. 3 is a longitudinal sectional view taken through the assembly.

DESCRIPTION OF INVENTION

Referring now to FIG. 1, there is shown an aroma-dispensing cartridge and holder assembly in accordance with the invention, the assembly being shown installed under the dashboard 10 of an automobile. It will be appreciated that this installation is merely by way of example; for in practice one may place the assembly under the desk in an office and in any other location where one wishes to charge the air of an interior with a fragrance to create a more pleasing atmosphere or for freshening the air, or for any other useful purpose that can be effected by the emission of an aroma.

The assembly includes a holder or socket 11 in the form of a receptacle having a generally rectangular cross-section, the sides of the holder beng profiled to define a pair of opposing channels 11A and 11B. The open mouth 12 of the holder faces the front seat of the vehicle so that it is readily accessible to the driver or a passenger. The upper edge of mouth 12 is provided with an upright flange 13 which, when the holder is installed, abuts the dashboard panel to resist displacement of the holder when a cartridge is inserted therein or when the head of an inserted cartridge is pressed in.

The assembly further includes a replaceable cartridge, generally designated by numeral 14, the cartridge comprising a bottle 15, a stopper 16 and a head 17. Bottle 15, which is filled with an appropriate liquid scent LS, has a generally rectangular cross-section and is provided at its sides with bulging tracks, only one of which, 15A, is shown in FIG. 2. These tracks have a formation complementing channels 11A and 11B, so that the tracks ride within these channels.

The base of bottle 15 is provided with a protuberance or plug 18 which passes through an opening 19 in the end wall of the holder, so that when a cartridge is inserted, it securely nests within the holder. In practice, holder 11 may be provided with a spring-operated reject mechanism (not shown) havng a button actuator which when pressed pushes the cartridge partly out of the holder to facilitate its removal.

Supported on stopper 16 is a suction pump which includes a hollow piston 20 that is axially shiftable. Piston 20 is normally maintained at its extended position in which its free end is projected beyond mouth 14 of holder 11 by a biasing spring 21. The other end of the plunger communicates with a flexible pipe 22 extending into the bottle 15 to draw fluid therefrom. The suction pump mechanism is of the type commonly used in household spray bottles such as those containing a window cleaner and sold commercially under the WINDEX trademark.

Stopper 16 is provided with a collar 23 which is concentric with plunger 20. Collar 23 telescopes within a sleeve 24 extending from the base 25 of actuator head 17 having an internal chamber 27 provided with an array of vent openings 28 on the upper wall of the head. Sleeve 24 has an internal ridge 24A formed at its open end. When head 17 is fully extended by plunger 20, ridge 24A engages an external abutment 23A formed at the open end of collar 23 to provide a limit preventing disengagement of the sleeve from the collar.

Occupying internal chamber 27 is a body or pad 29 of absorbent material, which in practice may be a flexible foam plastic or sponge-like material, or blotting paper. The free end of hollow plunger 20 is coupled to a center inlet 30 formed on the base 25 of the head, whereby the plunger communicates with the chamber.

The entire assembly may be molded or otherwise fabricated of a material such as polyethylene or PVC having adequate structural strength and chemically inert with respect to the liquid scent. To facilitate attachment, a pressure-sensitive adhesive layer 31 is bonded to the upper face of the holder, the layer having a peel-off protective cover 32. To install the holder, one simply removes cover 32 before pressing the adhesive layer against the underside of the dashboard or whatever other surface is to be used for the installation.

Operation

When head 17 is pressed in, this causes plunger 20 to make a forward stroke to activate the suction pump. Liquid drawn from pipe 22 in the bottle passes through hollow plunger 21 and is sprayed into the absorptive pad 29 in internal chamber 28. When the head is released, spring 21 then urges the plunger in the reverse stroke direction and returns the head to its initial position.

One may repeat this action several times to saturate the pad. Because the chamber is vented, an aroma therefrom is wafted into the interior. The lasting power of the aroma depends on several factors, such as the degree of ventilation in the interior, the concentration and character of the liquid scent and the nature of its carrier. One can, of course, when the aroma charge in the atmosphere becomes weak, again saturate the pad.

By providing the user with a set of several cartridges having a variety of scents, one gives him a range of choices. The user can withdraw a cartridge from the holder and replace it with another cartridge in a matter of seconds.

The cartridges, because they are molded of low-cost plastic material and include a pump of the type that can be inexpensively mass-produced, may be treated as a throw-away or disposable product. However, since in order to replenish the liquid scent one has only to pull off the cartridge stopper, cartridges may be refilled from a large supply bottle. In the case of insect-repellent, for example, it may be preferable to refill the cartridge from a supply.

While there has been shown and described a preferred embodiment of an aroma-dispensing cartridge and holder assembly in accordance with the invention, it will be appreciated that many changes and modifications may be made therein without, however, departing from the essential spirit thereof. Thus instead of a separate holder attachable to the underside of a dashboard, the holder may be integrated into the panel of the dashboard and become a permanent fixture thereof. Also, instead of a "Windex"type pump, one may use an atomizer pump of the type specifically designed for perfumes, such as that disclosed in the Boris U.S. Pat. No. 4,025,046.

I claim:

1. An aroma-dispensing cartridge and holder assembly comprising:

A a holder having an open mouth and a rear wall; and
 B a replaceable cartridge insertable in said holder, said cartridge being constituted by a bottle which is received within the holder with its base adjacent said rear wall, said bottle being fillable with liquid scent, a stopper for the bottle, a suction pump mounted on the stopper and provided with a pipe extending into the bottle and a hollow plunger which is axially shiftable, the free end of the plunger being coupled to the base of an actuating head which projects outside of said holder and is provided with a vented internal chamber in communication with said plunger, said chamber having an absorptive pad therein, whereby when the head is pressed in to cause the plunger to make a forward stroke, liquid scent drawn from said bottle passes through said plunger and is injected into said pad which then exudes an aroma through the chamber vent.

2. An assembly as set forth in claim 1, wherein said holder includes means to attach the holder to an interior whose atmosphere is to be charged with aroma.

3. An assembly as set forth in claim 1, wherein said holder and said cartridge bottle have matching, generally rectangular cross-sections and said head has a generally box-like formation, one of whose sides is provided with openings to vent the inner chamber defined by this formation.

4. An assembly as set forth in claim 3, wherein the opposing sides of said holder have a channel formation and the corresponding sides of said cartridge have a complementary track formation.

5. An assembly as set forth in claim 4, wherein said cartridge bottle has a protruding bottom plug which is received in an opening in the rear wall of the holder.

6. An assembly as set forth in claim 1, wherein said plunger is spring-biased to return the head to its initial position when the pressed-in head is released.

7. An assembly as set forth in claim 1, wherein said liquid scent is a perfume.

8. An assembly as set forth in claim 1, wherein said liquid scent is an air-freshener.

9. An assembly as set forth in claim 1, wherein said liquid scent is an insecticide.

10. An assembly as set forth in claim 2, wherein said attachment means is a layer of pressure-sensitive adhesive on the flat upper face of said holder.

* * * * *